United States Patent [19]

Sharma et al.

[11] Patent Number: 5,069,909
[45] Date of Patent: Dec. 3, 1991

[54] TRANSDERMAL ADMINISTRATION OF BUPRENORPHINE

[75] Inventors: Kuldeepak Sharma; Samir D. Roy, both of Mountain View; Eric J. Roos, Redwood City, all of Calif.

[73] Assignee: Cygnus Therapeutic Systems, Redwood City, Calif.

[21] Appl. No.: 540,908

[22] Filed: Jun. 20, 1990

[51] Int. Cl.$^5$ .............................................. A61F 13/00
[52] U.S. Cl. .................................... 424/449; 424/448; 514/947
[58] Field of Search ................................ 424/448, 449

[56] References Cited

U.S. PATENT DOCUMENTS

| | | | |
|---|---|---|---|
| 3,433,791 | 3/1969 | Bentley | 260/285 |
| 4,626,539 | 12/1986 | Aungst et al. | 514/282 |
| 4,806,341 | 2/1989 | Chien et al. | 424/448 |
| 4,956,171 | 9/1990 | Chang | 424/449 |

FOREIGN PATENT DOCUMENTS

| | | |
|---|---|---|
| 282156 | 9/1988 | European Pat. Off. |
| WO8801497 | 3/1988 | PCT Int'l Appl. |
| WO8809676 | 12/1988 | PCT Int'l Appl. |

OTHER PUBLICATIONS

Adriensen, H. et al., *Acta. Anaesthesia Belg.* (1985) 36:33-40.
Bickel, W. K. et al., *Chem. Pharmacol. Ther.* (1990) 43:72-78.
Bullingham, R. et al., *Clin. Pharmacol. Ther.* (1980) 28:667-72.
Bullingham, R. et al., *Clin. Pharmacol.* (1983) 8:332-43.
Bullingham, R. et al., *British Clin. Pharmacol.* (1982) 13:665-73.
Fudala, P. J. et al., *Clin. Pharmacol Ther.* (1990) 47:4:525-534.
Heel, R. C. et al., "Buprenorphine: A Review of Its Pharmacological Properties and Therapeutic Efficacy", *Drugs* (1979) 17:81-110.
O'Sullivan, G. H. et al., *Anaesthesia* (1983) 38:977-84.
Ostrowski, M. J. et al., *British J. Clin. Pharmacol.* (1979) 33:587-90.
Rosana, C. et al., *Clin. Ther.* (1982) 5:61-8.
*Martindale: The Extra Pharmacopeia,* Entry 6209-w (Buprenorphine Hydrochloride), London: The Pharmaceutical Press, 1989.
*Physician's Desk Reference,* 43rd Edition, pp. 1476-1477 ("Buprenex") (1989).

*Primary Examiner*—Thurman K. Page
*Assistant Examiner*—D. Gabrielle Phelan
*Attorney, Agent, or Firm*—Dianne E. Reed

[57] ABSTRACT

Method and laminated composite for administering buprenorphine transdermally to treat pain. The composite comprises an impermeable backing layer and a reservoir layer containing buprenorphine and optionally a permeation enhancer combined with a pressure-sensitive adhesive with the amounts of buprenorphine and optional enhancer being sufficient to cause the buprenorphine to pass through the skin at a rate in excess of about 0.05 mcg/cm$^2$/hr.

6 Claims, 1 Drawing Sheet

TRANSDERMAL ADMINISTRATION OF BUPRENORPHINE

BACKGROUND OF THE INVENTION

1. Field of the Invention

This invention relates to the transdermal administration of effective dose levels of buprenorphine to patients. More particularly, it relates to transdermal dosage forms for buprenorphine and to their use.

2. Prior Art

Buprenorphine is the common name for (5α, 7α (s))-17-cyclopropylmethyl)-α-(1,1-dimethylethyl)-4,5-epoxy-18,19-dihydro-3-hydroxy-6-methoxy-α-methyl-6,14-ethenomorphinan-7-methanol. This material is sold under the trademarks Buprenex (Morton-Norwich) and Tengesic (Reckitt and Coleman). It is described in U.S. Pat. No. 3,433,791 (1968). It is an analgesic which demonstrates narcotic agonist-antagonist properties. It has been used principally for the management of pain associated with surgical procedures, cancer, accidental trauma, and myocardial infarction. Buprenorphine is also being used in the detoxification treatment of heroin addicts due to its narcotic agonist/antagonist properties. Bickel, W. K., et al., *Chem. Pharmacol. Ther.* (1988)43:1:72–78 and Fudala, P. J., et al., *Clin. Pharmacol. Ther.* (1990)47:4:525–534.

Heretofore, buprenorphine has been administered most commonly by intramuscular injection or intravenous injection as reported by Norwich Eaton Pharmaceuticals, Inc., in "Buprenex Prescribing Information," Norwich, N.Y., 1986; "Buprenex Compatibility Chart," Norwich, N.Y., 1986; and "Buprenex: Background Data for Review for Pharmacy and Therapeutic Committees," Norwich, N.Y., May 1985. See also, Heel, R. C., et al., "Buprenorphine : A Review of Its Pharmacological Properties and Therapeutic Efficacy," *Drugs* (1979) 17:81–110.

In view of the chronic nature of many of the severe conditions for which buprenorphine is employed, it can often be desired to administer this drug over a prolonged period of time. To that end, the Norwich Eaton publications mention the possibility of slow, prolonged IV administration and Robbie, D. S., has published the results of a trial of sublingual buprenorphine in chronic cancer pain settings in *British J. Clin. Pharmacol.* (1979) 33:587–90. Additional discussions of sublingual administration of buprenorphine include: Bullingham, R., et al., *Clin. Pharmcol. Ther.* (1980) 28:667–72; Bullingham, R., et al., *Clin. Pharmacol.* (1983) 8:332–43; Bullingham, R., et al., *British Clin. Pharmacol.* (1982) 13:665–73; Rosana, C., et al., *Clin. Ther.* (1982) 5:61–8; O'Sullivan, G. H., et al., *Anaesthesia* (1983) 38:977–84; and Adriensen, H., et al, *Acta. Anaesthesia Belg.* (1985) 36:33–40.

The possibility of transdermal administration of buprenorphine has also been postulated. PCT published Patent Application No. WO88/09676 (Warner Lambert, published 15 Dec. 1988) is directed to the use of fatty acids or fatty acid esters as transdermal drug delivery enhancers and mentions buprenorphine as one of the drugs with which these enhancers might be used. A similar suggestion may be found in U.S. Pat. No. 4,626,539, issued 2 Dec. 1986 to B. Aungst, et al. European Patent Application No. 0,282,156 (Alza Corp., 14 Sept. 1988) teaches that transdermal coadministration of corticosteroids with irritating drugs is advantageous and lists buprenorphine as a drug which might benefit from such coadministration. PCT Patent Application WO88/01497 (Rutgers, The State University of New Jersey, 10 Mar. 1988) and the corresponding U.S. Patent No. 4,806,341, issued Feb. 21, 1989, are directed to a transdermal morphinan narcotic analgesic or antagonist dosage unit and propose buprenophine as a possible drug for inclusion. With the possible exception of the WO88/01497 reference and its United States counterpart, which include a pro forma hypothetical example to a buprenophine transdermal system, none of these references has any examples which actually purport to demonstrate transdermal administration of buprenophine and no data relating to the flux of buprenophine through the skin are provided. Therefore, at best, this art is a speculative teaching that leaves the reader with the task of experimenting to find out whether or not it is possible to administer buprenophine transdermally in vivo at therapeutically effective rates.

Statement of the Invention

It has now been found that one can actually achieve noninvasive sustained administration of buprenorphine at therapeutically effective dose levels by continuously delivering it transdermally from a laminated composite patch affixed to the patient's skin.

Thus, in one aspect, this invention provides a method for transdermal buprenorphine administration. This method can take the form of applying buprenorphine to a predetermined area of the patient's skin adequate to enable the buprenorphine to permeate the area of skin at a rate in excess of about 1 microgram per hour.

In another aspect, the buprenorphine is administered with a permeation enhancer, either concurrently or sequentially.

In yet another aspect, the administration is accomplished by affixing to the patient's skin a transdermal buprenorphine delivery system, which has a contact area with the patient's skin of from 10 to 100 cm$^2$ and which makes buprenorphine available to the area of skin for transdermal administration at a rate in excess of 0.05 micrograms per cm$^2$ per hour. Preferred administration rates are from about 0.05 to about 5.0 micrograms per cm$^2$ per hour.

In more specialized aspect, the buprenorphine is present in the system dissolved in a layer of pressure sensitive adhesive with or without permeation enhancer.

In yet other aspects, the invention provides the delivery system to carry out these processes and achieve effective transdermal buprenorphine delivery.

Brief Description of the Drawing

The drawing shows in cross-section an embodiment of a skin patch for administering buprenorphine transdermally.

MODES FOR CARRYING OUT THE INVENTION

Definitions

Figure 1:
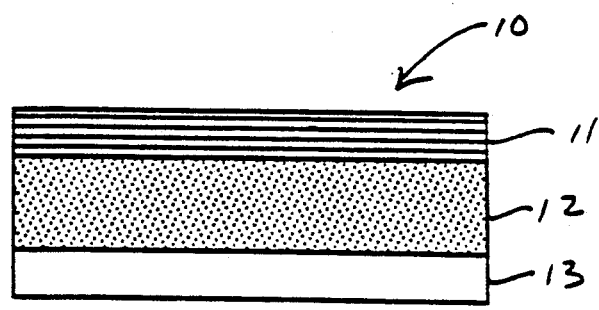

In describing and claiming the present invention, the following terminology will be used in accordance with the definitions set out below.

"Buprenorphine" shall mean (5α, 7α (s))-17-(cyclopropylmethyl)-α (1,1-dimethylethyl)-4,5-epoxy18,19-dihydro-3-hydroxy-6-methoxy-α-methyl-6,14-ethenomorphinan-7-methanol. As used herein, the term encompasses the free base and the acid addition salts such as the hydrochloride.

"Penetration enhancement" or "permeation enhancement" as used herein relates to an increase in the permeability of skin to a buprenorphine pharmacologically active agent, i.e., so as to increase the rate at which buprenorphine permeates into and through the skin. A "permeation enhancer" is a material which achieves permeation enhancement of buprenorphine.

"Transdermal" (or "percutaneous") shall mean passage of a material into and through the skin to achieve effective therapeutic blood levels or deep tissue therapeutic levels. Transdermal delivery is to be distinguished from "topical" delivery. By "topical" administration is meant local administration of a topical pharmacologically active agent to the skin as in, for example, the treatment of various skin disorders or the administration of a local anaesthetic. "Topical" delivery can involve penetration of a drug into the skin but not through it, i.e., topical administration does not involve actual passage of a drug into the bloodstream.

"Carriers" or "vehicles" as used herein refer to carrier materials without pharmacological activity which are suitable for administration with other pharmaceutically active materials, and include any such materials known in the art, e.g., any liquid, gel, solvent, liquid diluent, solubilizer, or the like, which is nontoxic and which does not interact with the drug to be administered in a deleterious manner. Examples of suitable carriers for use herein include water, mineral oil, silicone, inorganic gels, aqueous emulsions, liquid sugars, waxes, petroleum jelly, and a variety of other oils and polymeric materials.

By a "therapeutically effective" amount of buprenorphine is meant a nontoxic but sufficient amount of buprenorphine to provide the desired therapeutic effect. The desired therapeutic effect is the alleviation of pain or inducement of analgesia in the patient or in the case of heroin addicts, the achievement of detoxification.

The present invention involves the transdermal administration of buprenorphine. This mode of administration may be carried out by affixing a buprenorphine-containing laminated composite to the patient's skin.

A representative laminated composite for administering buprenorphine transdermally to humans to induce analgesia is shown in the drawing. This composite, generally designated 10, comprises a backing lamina 11, a buprenorphine reservoir lamina 12, and a release liner lamina 13.

The backing layer provides a protective covering for the composite and may itself be a single layer or a multiplicity of layers. For instance if the composite is to be worn for periods in excess of a day or two, it is desirable to make the backing from an elastomeric polymer such as polyurethane, polyether amide, or copolyester. In order to insure the occlusiveness of such elastomeric polymers, it may be necessary to place a layer of an occlusive material, such as polyisobutene, between the backing and the reservoir. For devices that are intended to be worn for shorter durations, the backing may be made from relatively flexible but not elastomeric occlusive polymers such as polyester, polyethylene, or polypropylene. The thickness of the backing layer will normally be in the range of about 15 microns to about 250 microns.

The reservoir lamina is composed, in its most elementary form, of buprenorphine (base or HCl) in the amount of 1 to 12% by weight (preferably 2 to 10% by weight) and a pressure-sensitive adhesive. The pressure-sensitive adhesive is generally a material such as an isobutylene, a silicone, or an acrylate adhesive. Representative adhesives include: polyisobutylene; silicone adhesives such as silastic, Dow Corning X7-2920 silicone adhesive or Dow Corning 2675 silicone adhesive, with or without added silicone-oil tackifier; and solvent-based or water-based acrylate materials. Acrylate copolymer materials are available commercially. For example, Monsanto Chemical Company distributes a family of vinyl acetate-acrylate copolymer resin solutions under the trademarks GELVA ® 737 and GELVA ® 788 and Morton Thiokol, Inc. distributes acrylate copolymers under the trademarks Morstik 207A and Morstik 607.

These acrylate copolymer materials can be used separately or in mixtures. Several specific materials which give good results are the Morstik 607 materials, the GELVA ® materials, which are believed to be based on 2-ethylhexyl acrylate, and mixtures of from about 20:1 to about 1:1 GELVA ® 737 and GELVA ® 788 (ratios given as weight ratios of GELVA ® 737 to GELVA ® 788). All of these materials are solvent based but form films following casting and removal of the solvent. The term "solid" is used broadly since the "solid" product is generally a tacky, amorphous (i.e. pressure sensitive adhesive) non-flowing material.

These materials are typically available as solutions in organic solvents such as toluene, ethanol, isopropanol, ethyl acetate and the like. These solvents are substantially eliminated from the matrix during fabrication. In addition, one can use water-based acrylate adhesives such as GELVA ® 2333 or Flexcryl 1625. These materials are available as emulsions in water and are preferred because of their environmental safety and their use on human skin and because they give high skin fluxes of buprenorphine. Other similar water-based acrylate adhesive polymers can be used as well.

These matrix materials have the property of being high tack pressure-sensitive adhesives when dried and/or cured. Thus, the matrices formed from these materials can adhere directly to the patient's skin without the need for additional separate adhesives.

An optional third component of the reservoir lamina is one or more permeation enhancers. The enhancer is present in the layer is amounts ranging up to about 25% by weight. Preferred use levels are from 2% to 20% and especially 5% to 20% by weight. Representative enhancers are esters of the formula $[CH_3(CH_2)_mCOO]_nR$ in which m is an integer from 8 to 16, preferably 8 to 12, most preferably 10; n is 1 or 2, preferably 1; and R is a lower alkyl ($C_1$–$C_3$) residue which may be substituted with 0 to 2 hydroxyl groups, or a mixture of such an ester or methyl laurate and diethylene glycol monomethyl or monoethyl ether. The volume ratios of ester to ether in such mixtures will normally be in the range of 90:10 to 50:50. The use of such mixtures as permeation enhancers is described in commonly owned co-pending U.S. patent application Ser. No. 327312, filed 22 Mar. 1989. The preferred esters of the above formula are lower alkyl ($C_1$–$C_3$) esters of lauric acid, with propylene glycol monolaurate (PGML) being particularly preferred. It will be appreciated by those skilled in the art that commercially available PGML is normally a mixture of propylene glycol monolaurate, propylene glycol dilaurate and either propylene glycol or methyl laurate or both. Thus "propylene glycol monolaurate" is intended to encompass the pure compound as well as the mixture that is sold commercially. It is also intended that the enhancer may be composed of a mixture of said esters, by themselves or in combination, with one or both of the mentioned ethers. Other enhancers which may be employed to advantage include diethylene glycol monomethyl and monoethyl ethers, lauric acid, lauric alcohol, capric acid, oleic acid, glycerol oleate, and the like. In using some of these materials care must be taken to avoid irritation which may accompany these materials at high use levels.

The thickness of the reservoir layer will normally be in the range of 20 microns to 150 microns, preferably 25 microns to 100 microns.

The reservoir lamina plays two functional roles, namely, it is a reservoir for buprenorphine and the solvent/enhancer, and because of its composition, it is adhesive and its basal surface provides the means by which the composite is affixed to the skin. The basal release liner lamina 13 is a protective coating for the reservoir lamina during storage and prior to affixation to the skin. This layer is removed from the composite before the composite is affixed to the skin.

The reservoir layer may be formulated by conventional methods known int he field of transdermal drug delivery devices and the three layers assembled into a laminated composite by the like methods. These methods and specific embodiments of the invention are further illustrated by the following Experimental Results and Examples. These examples are not intended to limit the invention in any manner.

This invention will be further described with reference to the following Experimental Results and Examples. The Experimental Results section provides details of the methodology employed. The Examples describe the production and testing of specific buprenorphine delivery devices.

Experimental Results

Preparation of Buprenorphine Base: Buprenorphine base was prepared from its HCl salt. A known amount of commercial buprenorphine HCl was dissolved in water, followed by the addition of saturated solution of $Na_2HCO_3$, to precipitate buprenorphine base. The precipitate was then filtered and washed several times with cold deionized water to remove excess $Na_2HCO_3$. The white residue was then dried overnight in air. The dried residue was added to a water:ethanol (80:20) mixture, and heated to 60° C., to dissolve the free base, followed by immediate filtration. Upon cooling, the buprenorphine base crystallized. The rhombic shaped crystalline product was then filtered and dried under a gentle stream of nitrogen. The purity of the base was checked by melting point and HPLC assay. The melting point of the base was 210° C., virtually the same as reported in the literature. The purity of the base by HPLC assay was 99%.

Solubility Determination: The solubility of buprenorphine base and HCl salt in various vehicles was obtained by equilibrating a large excess of solute with the vehicle in a water-jacketed glass container. Temperature was maintained at 32° C. by a constant temperature water bath and vigorous mixing with a magnetic stirring bar. Equilibrium time for all the studies was $\geq 48$ hr. An excess of solute was always present in the slurries. Samples were taken, filtered through glass wool-tipped pipets, and an appropriate volume of filtrate was diluted with acetonitrile and assayed by HPLC. The procedure was repeated three times and an average value calculated.

Skin Preparation: Human cadaver skin was used for permeation studies. Frozen skins were thawed and epidermal layers (stratum corneum+viable epidermis) separated from dermatomed skin by immersion in water at 60° C. for 2 minutes. The heat-separated epidermal layer was used for studies or stored at $-20°$ C. for later studies.

Skin Permeation Method:

Flow-Through Cells:

The flow-through diffusion cells (LGA) have a 7.5 ml receiver compartment and an inlet and outlet to allow flow of solvent. The receptor fluid (phosphate buffer at pH 6.0) was pumped from a temperature-controlled reservoir into and through the cell by a peristaltic pump, and collected in test tubes situated in an automatic fraction collector. The collector allows for simultaneous collection from a number of cells and replacement of test tubes with a fresh set at predetermined intervals. Both the Franz cells and the flow-through cells were made up of glass and were jacketed for temperature control. 250 microL of suspension of buprenorphine in a vehicle was used as the donor phase.

Static Cells: In some experiments, static, side-by-side diffusion cells were used. Skin sections were mounted carefully between the half-cells of the diffusion cell and fastened with a rigid clamp. The receiver compartment was filled with phosphate buffer of pH 6.0 (isotonic). The doner compartment was charged with a saturated solution of buprenorphine in an appropriate vehicle or enhancer. The diffusion cells were placed in an oven and the temperature of the diffusion cell contents was maintained at 32° C. Stirring was set at 200 rpm throughout the experiment. At predetermined times, either one ml of receiver content was withdrawn and replaced with previously warmed (32° C.) fresh receiver fluid or the whole receiver contents were emptied and replaced with fresh receiver fluid. Samples were taken from the doner compartment at the beginning of the experiment to determine the concentration of drug. The samples were assayed by HPLC.

Assay Procedure: Buprenorphine was assayed by HPLC using UV-detection at 210 nm. A $\mu$-Bondapak $C_{18}$ column with acetonitrile-buffer pH 5.0 (45:55) as a mobile phase was used for chromatographic resolution. Calibration curves were obtained by plotting the peak height or area of the authentic drug as a function of drug concentration. Standard curves demonstrated linearity over the concentration range encountered in samples.

Data Analysis: Skin flux was determined from the following equation:

$$\frac{dM}{dt} = J = P \cdot \Delta C$$

where J is the skin flux, P is the permeability coefficient and $\Delta C$ is the concentration gradient across the membrane, which is assumed to be the same as the doner concentration. The skin flux was determined from the slope of the plot of cumulative amount of buprenorphine permeated (M) versus time (t).

Pharmacokinetics of Buprenorphine: The basic pharmocokinetic parameters for buprenorphine are summarized in Table 1.

TABLE 1

| Pharmacokinetics of Buprenorphine[1] | |
|---|---|
| Parameter | |
| Daily dose | 1.2 mg/day (i.v., tid) |
| $T_{\frac{1}{2}}\beta$ | 3.1 ± 0.6 h |
| $Cl_T$ | 77 ± 5 L/h |
| $V_{dss}$ | 188 ± 35 L |
| MEC (analgesics) | 0.5 to 0.7 ng/ml |
| $K_o$ ($J_{skin}$) | 38 to 54 μg/h |
| Desired delivery rate from 20 cm² patch | 1.9 to 2.7 μg/cm²/h |

[1] Roy S. Bullingham et al. Br. J. Clin. Pharmac. 13:665-673 (1982).

Based on these values, the input rate or percutaneous absorption rate ($J_{skin}$) was calculated from $Cl_T$ times $C_{ss}$. This value and the desired delivery rate as calculated are also presented in Table 1.

Physicochemical Properties: In determining whether or not buprenorphine could be administered transdermally and what type of materials (vehicles, polymer matrices, etc.) were likely candidates for use as adjuncts to this administration, basic solubility and permeability studies were carried out.

Solubility Studies: The studies of buprenorphine base in deionized water (0.008 mg/ml) was considerably lower than that of buprenorphine HCl (12 mg/ml). The octanol-water partition coefficient ($K_{o/w}$) of the base form (1217) was higher than that of the HCl salt (427), thereby indicating that the base is more lipophilic than the salt form.

The solubilities of the base and HCl salt in various vehicles is summarized in Table 2.

TABLE 2

Solubility of Buprenorphine base and HCl in various vehicles at 32° C.

| Vehicle | Solubility (mg/ml) Base | HCl |
|---|---|---|
| Propylene Glycol | 5.1 | 22.5 |
| Water | 0.008 | 12.0 |
| Ethanol (absolute) | 58.4 | |
| Isopropyl myristate | 13.3 | |
| Transcutol | 88.6 | |
| Propylene glycol-monolaurate | 37.9 | |

The maximum base solubility of 88.6 mg/ml was obtained in Transcutol ®. The HCl salt's solubility in propylene glycol was considerably higher than the free base form's.

In Vitro Skin Permeation: Permeation of buprenorphine base through cadaver skin from saturated solution is summarized in Table 3.

TABLE 3

Buprenorphine (base) skin flux from saturated solution using flow-through cells

| Formulation (% composition) | n | $J_{skin}$ (μg/cm²/h) |
|---|---|---|
| PG (100) | 3 | 0.35 ± 0.06 |
| PG/Oleic acid (90:10) | 3 | 2.2 ± 0.6 |
| PG/PGML (90:10) | 3 | 2.6 ± 0.2 |
| PG/Glyceryl Oleaate (90:10) | 3 | 1.5 ± 0.3 |
| PG/Transcutol (90:10) | 3 | 0.19 ± 0.02 |
| PG/Methyl laurate (90:10) | 3 | 2.8 ± 1.0 |
| PG/DMSO (50:50) | 3 | 1.9 ± 1.0 |
| PG/Ethanol (90:10) | 3 | 0.28 ± 0.3 |

PG = Propylene glycol;
PGML = Propylene glycol monolaurate;
DMSO = Dimethyl sulfoxide Skin flux from pure propylene glycol, which also acted as a control, was considerably lower than other studied formulations. The skin fluxes from the formulations containing oleic acid, propylene glycol monolaurate and methyl laurate, each separately dissolved in propylene glycol, were 2.2±0.06, 2.6±0.2 and 2.8±1.0 microg/cm²/h, respectively.

Permeation of buprenorphine base as a function of aqueous pH at 32° C. is shown in Table 4.

TABLE 4

Permeation of buprenorphine base as a function aqueous pH

| Equilibrium pH | $C_s$ (mg/ml) | n | $J_{skin}$ (μg/cm²/h) | P[1] (cm/h) |
|---|---|---|---|---|
| 5.0 | 0.692 | 3 | 0.59 ± 0.13 | $8.7 \times 10^{-4}$ |
| 6.0 | 0.082 | 3 | 0.48 ± 0.02 | $5.9 \times 10^{-3}$ |
| 7.0 | 0.006 | 3 | 0.14 ± 0.01 | $2.3 \times 10^{-2}$ |
| 7.9 | 0.0006 | 3 | 0.05 ± 0.02 | $8.3 \times 10^{-2}$ |
| 8.7 | 0.00014 | 3 | 0.03 ± 0.01 | $2.1 \times 10^{-1}$ |

[1] $P = J/C_s$

Solubility of the base decreases exponentially as the pH increases. Buprenorphine skin flux increased as the pH was decreased to 5. These results indicate that the completely ionized form (pKa=8.4) of drug (pH=5.0) has higher skin flux than the partially un-ionized form; therefore, further permeation studies were performed using HCl salt as a permeating species. Nevertheless, the permeability coefficients increased as the pH was raised to 8.7, which is consistent with literature reports.

Buprenorphine base and HCl skin fluxes from mixed solutions were compared, and the data are summarized in Table 5.

TABLE 5

Buprenorphine skin flux from saturated solutions using flow-through cells.

| Formulation (composition) | saturation species | n | $J_{skin}$ (μg/cm²/h) |
|---|---|---|---|
| PG/LA (9:1) | base | 3 | 2.4 ± 1.2 |
| PG/LA (9:1) | HCl | 3 | 8.2 ± 3.6 |
| PG/H₂O/LA (9:0.95:0.5) | base | 3 | 1.9 ± 0.4 |
| PG/H₂O/LA (9:9.5:0.5) | HCl | 2 | 3.3 (3.3, 3.0) |
| PG/LAL (8:2) | HCl | 3 | 21.3 ± 6.7 |
| PG/LAL/EtOH (8:1.5:0.5) | HCl | 3 | 12.8 ± 5.0 |
| PG/H₂O/CA (8:1.5:0.5) | HCl | 2 | 12.5 (12.9, 12.1) |

PG = Propylene glycol;
LA = Lauric acid;
LAL = Lauryl alcohol;
EtOH = Ethanol;
CA = Capric acid.

On the average, buprenorphine HCl showed relatively higher penetration than the base form. The formulation containing 20% lauryl alcohol in propylene glycol gave the highest skin flux (21.3±6.7 microg/cm²/h). Capric acid appeared to be a better penetration enhancer than lauric acid, as shown in Table 5.

Permeation of buprenorphine HCl from various formulations containing penetration enhancers in propylene glycol is summarized in Table 6.

TABLE 6

Buprenorphine HCl skin flux from various formulations (saturated solution) using flow-through cells at 32° C.

| Formulation (% composition) | n | $J_{skin}$ (μg/cm²/h) |
|---|---|---|
| PG (100)[1](control) | 2 | 0.27 (0.26, 0.28) |
| PG/LINOA/H₂O (90:15:5) | 2 | 1.8 (1.9, 1.7) |
| PG/LAL/H₂O (90:17:3) | 3 | 15.9 ± 4 |
| PG/LAL/EtOH (80:15:5) | 3 | 20.3 ± 2.6 |
| PG/PGML/H₂O (80:15:5) | 3 | 29.7 ± 9.7 |
| PG/MA/EtOH (80:15:5) | 2 | 5.7 (7.1, 4.4) |

TABLE 6-continued

Buprenorphine HCl skin flux from various formulations (saturated solution) using flow-through cells at 32° C.

| Formulation (% composition) | n | $J_{skin}$ ($\mu g/cm^2/h$) |
|---|---|---|
| PG/NA/H$_2$O (80:15:5) | 2 | 3.7 (3.4, 4.0) |
| PG/LA/PGML(S) (82:3:15) | 3 | 12.9 ± 2.3 |
| PG/LAL/PGML(S) (80:3:17) | 3 | 9.0 ± 2.8 |
| PGML (S) [100][1] | 3 | 0.63 (0.66, 0.63) |
| Ethanol (100)[1] | 1 | 1.9 |

PG = Propylene glycol;
LA = Lauric acid;
LAL = Lauryl alcohol;
EtOH = Ethanol;
LINOA = Linolenic acid;
MA = Myristic acid;
NA = Nanoic acid;
PGML = Propylene glycol monolaurate.
[1]Static cells (side-by-side diffusion cells).

Formulations containing lauryl alcohol and lauric acid exhibited the highest skin flux among the studied formulations. Skin flux of buprenorphine HCl from pure propylene glycol served as a control. PGML (commercial grade) increased the skin flux by 2-fold. It should be noted that the skin flux from the formulation containing PG/PGML/water (8:15:5) was considerably higher than those of the other studied formulations.

In order to determine the principal diffusional barrier of skin in transporting both base and HCl salt across the membrane, the permeating of drug through heat-separated epidermis was compared with stripped epidermis. Stripping removes most of the stratum corneum. The skin was stripped with Scotch brand cellophane tape to remove stratum corneum twenty times. Permeations of the base and the HCl salt through heat-separated epidermis and stripped epidermis from saturated aqueous solution at 32° C. are shown in Table 7.

TABLE 7

Permeation of buprenorphine base and HCl salt through stripped and heat-separated epidermis from aqueous (deionized water) saturated solution at 32° C.[1]

| Saturation species | Skin Type | n | $J_{skin}$ ($\mu g/cm^2/h$) |
|---|---|---|---|
| Buprenorphine | Epidermis | 2 | 0.37 (0.35, 0.39) |
| Buprenorphine | Stripped | 3 | 2.2 ± 0.3 |
| Buprenorphine HCl | Epidermis | 2 | 2.1 (2.4, 1.7) |
| Buprenorphine HCl | Stripped | 3 | 20.5 ± 4.3 |

[1]Side-by-side diffusion cells

On the average, skin flux for the HCl salt is higher than that of the base form. Skin flux increased by 6- and 10-fold for the base and the HCl salt, respectively, upon stripping, thereby indicating that stratum corneum acts as a barrier for the transport of these molecules across the membrane. Since buprenorphine base skin flux increased only by 6-fold upon stripping, it appears that viable epidermis which is a hydrogel in nature, offered a diffusional barrier for buprenorphine base, since the base is highly lipophilic as compared to the HCl salt.

Buprenorphine Transdermal Administration System Without Vehicles (Examples 1-4)

The systems of these Examples are matrix-type monolithic (i.e., there is no rate controlling membrane laminated to a backing). The drug release is controlled by the monolith and the skin. Various polymer combinations are used. The drug is uniformly mixed in these polymer mixtures and then case. Solvent is then removed and a backing layer is affixed.

Example 1

5% Buprenorphine HCl-Silicone Patch

A series of buprenorphine HCl delivery systems were prepared by the following procedure: 5% Buprenorphine HCl was mixed with silicone adhesive polymer (Dow Corning silicone #2675) in freon (50% wt) and rotated using a vortex for 4 hours. The drug-polymer homogeneous mixture was then cast on a polyester film (#1022 release liner) with a 10 mil Gardener knife. The solvent in the polymer system was evaporated in a 75° C. oven for 30 min. The resulting polymer film was laminated with another polyester film (#1022). The same method was used to prepare a 2% buprenorphine HCl-silastic (#2920) system. 3 cm$^2$ sections were cut from the film for testing.

Modified Franz cells wee used for in vitro skin flux experiments. The release liners were removed. The polymer systems that were made were then laminated on the stratum corneum of human cadaver skin, mounted between the two half-cells and fastened with a clamp. The receiver compartment was filled with phosphate buffer saline solution pH 6.0 containing 0.01% NaN$_3$. The volume of the receiver compartment was 7.5 ml. Samples were taken at 4, 8, 12, 24, 36 and 48 hour intervals by withdrawing 1 ml of receiver fluid. The sample receiver fluid (1 ml) was replaced with fresh receiver fluid. The flux was calculated from the slope of the cumulative amount of buprenorphine HCl in the receiver compartment vs. time. Three experiments for each system were conducted.

The average skin flux of buprenorphine HCl from 5% buprenorphine HCl silicone 2675 and 5% buprenorphine HCl silicone 2920 was 0.06±0.01 and 0.09±0.02 microg/cm$^2$/hr, respectively. The average cumulative amount of buprenorphine HCl released after 48 hours from these systems was 2.45±0.50 and 3.77±0.80 microg/m$^2$, respectively.

Example 2

5% Buprenorphine HCl-PIB Patches

A series of buprenorphine HCl-PIB systems were prepared by the following procedure: 2% buprenorphine HCl was mixed with polyisobutylene (PIB) (1:5:1) solution in hexane (30% wt %) and rotated for 4 hours. The drug-polymer mixture was than cast on polyester film (#1022 release liner) with a 10 ml knife. The solvent in the mixture was evaporated in a 75° C. oven for 1 hour. The resulting polymer film was laminated with another polyester film (#1022). The same procedure was used to prepare a 2% buprenorphine HCl-PIB (1:5:3) system.

An in vitro skin flux experiment was conducted following the same procedure as explained in Example 1.

The average flux of buprenorphine HCl from 2% buprenorphine HCl-PIB (1:5:1) and 2% buprenorphine HCl-PIB (1:5:3) systems was 0.007±0.0001 and 0.08±0.002 microg/cm$^2$/hr. The average cumulative amount of buprenorphine HCl released after 48 hours from these systems was 5.17±0.73 and 5.20±0.70 microg/cm$^2$, respectively.

Example 3

2% Buprenorphine HCl-Acrylate Patches

A series of 2% buprenorphine HCl-acrylate patches was prepared by the following procedure: 2% of buprenorphine HCl was mixed with solvent-base acrylate Morstik (42% solid) and rotated for 2 hours. The drug polymer mixture was than cast on polyester film (#1022 release liner) with a 10 mil knife. The solvent in the polymer was evaporated in a 75° C. oven for 1 hour. The resulting polymer film was laminated with another polyester film (#1022). The same procedure was followed to prepare 2% buprenorphine HCl-water-base acrylate system. Gelva 2333 (52% solid % wt) was used as the acrylate in this case.

An in vitro skin flux experiment was conducted following the same procedure as explained in Example 1.

The average flux of buprenorphine HCl from 2% buprenorphine HCl-water-base acrylate and 2% buprenorphine HCl-solvent-base acrylate was $0.149 \pm 0.015$ and $0.012 \pm 0.003$ microg/cm$^2$/hr. The average total cumulative amount of buprenorphine HCl released after 48 hours from these systems was $7.07 \pm 1.2$ and $0.78 \pm 0.26$ microg/cm$^2$, respectively.

Based on the results seen in Examples 1 and 2, water-base acrylate was selected for optimisation as a buprenorphine HCl patch material.

Example 4

Optimization of Buprenorphine-Acrylate Patch

A series of 5% buprenorphine-acrylate patches was prepared by the following procedure: the 5% buprenorphine HCl was mixed and sonicated with about 3 ml of ethanol for 10 minutes. This drug-ethanol mixture was mixed with water-base acrylate Flexcryl 1625 (70% solid in water emulsion) and rotated for 3 hours. The ethanol is used for solubilizing and uniformly distributing buprenorphine HCl in the polymer. The drug-ethanol-polymer mixture was than cast on a polymer film (#1022 release liner) with a 10 mil knife. The ethanol and water in the polymer system were evaporated in a 75° oven for 2 hours. The resulting polymer film was laminated with another polyester film (#1022). The same procedure was used for the solvent-based acrylate patch.

The in vitro skin flux experiment was conducted following the same procedure as explained in Example 1.

The average flux of buprenorphine HCl from 5% buprenorphine HCl-water-base acrylate, Flexcryl 1625 and 5% buprenorphine HCl solvent-base Morstil acrylate was $0.76 \pm 0.2$ and $0.10 \pm 0.01$ microg/cm$^2$/hr. The average cumulative buprenorphine HCl released after 48 hours was $33.69 \pm 10.16$ and $3.77 \pm 0.80$ microg/cm$^2$, respectively. Based on this example, it is possible to achieve therapeutic blood levels with 5% buprenorphine HCl-Flexcryl 1625 patch of about 50 to 60 cm$^2$.

Buprenorphine Delivery Systems With Enhancers (Examples 5-7)

In this system, combinations of vehicles were used to achieve a therapeutic blood level. These patches were fabricated by mixing buprenorphine with vehicles and polymer solution/suspension. This mixture was cast on release liner. The solvent was removed and a backing was applied.

Example 5

2% Buprenorphine HCl—2% Enhancer—Water-based Acrylate

A series of 2% buprenorphine HCl-water-base acrylate systems with and without enhancers were prepared by the following procedures: 2% buprenorphine HCl was mixed with the appropriate amount of the enhancer-polymer mixture and rotated for 4 hours. The drug-enhancer-polymer mixture was than cast on a polyester film (#1022 release liner) with a 10 ml knife. The solvent in the polymer system was evaporated in a 75° C. oven. The resulting polymer film was laminated with another polyester film. The composition of each system is shown in Table 8.

TABLE 8

Flux and cumulative amount of buprenorphine HCl from water-base acrylate matrix through human cadaver skin.

| Patch # | Patch Composition | Flux ($\mu$g/cm$^2$/hr) | Cumulative Amount of Bup-HCl after 48 hours ($\mu$g/hr) |
|---|---|---|---|
| 1 | 2% Bup-HCl-98% water-base acrylate | 0.05 ± 0.002 | 2.06 ± 0.12 |
| 2 | 2% Bup + 2% Capric Acid + 96% Polymer | 0.16 ± 0.01 | 6.97 ± 0.45 |
| 3 | 2% Bup-HCl + 2% Oleic Acid + 96% Polymer | 0.18 ± 0.03 | 7.98 ± 1.45 |
| 4 | 2% Bup-HCl + 2% Softigen 767 + 96% Polymer | 0.19 ± 0.01 | 8.54 ± 0.19 |
| 5 | 2% Bup-HCl + 2% Transcutol + 96% Polymer | 0.03 ± 0.001 | 1.21 ± 0.08 |

An in vitro skin flux experiment was conducted following the same procedure as explained in Example 1.

The average flux and cumulative amount of buprenorphine HCl released after 48 hours is tabulated in Table 8. The flux and cumulative amount of buprenorphine HCl increased significantly in systems containing 2% capric acid, 2%. oleic acid and 2% Softigen 767. The flux and cumulative amount of buprenorphine HCl can be further increased by increasing the buprenorphine HCl and enhancer concentrations in the system. Softigen 767 is a water-soluble mixture of partial glycerides of natural, saturated vegetable fatty acids of an even-numbered chain length $C_8$-$C_1$.

Example 6

2% Buprenorphine + 2% Enhancer + 6% PGML—Water-based Acrylate

A series of 2% buprenorphine + 2% enhancer + 2% PGML water-base acrylate patches were prepared by the following procedure: The 2% buprenorphine HCl was mixed and sonicated with 6% PGML for 10 minutes. The appropriate amount of the drug-enhancer mixture was then added to a solution of water-based acrylate and rotated for 4 hours. The drug-PGML-enhancer-polymer mixture as than cast on a polyester film (#1022 release liner) with a 10 mil knife. The solvent in the polymer system was evaporated in a 75° C. oven for 2 hours. The resulting polymer films were laminated with another polyester film. The composition of each system is shown in Table 9.

TABLE 9

Flux and cumulative amount of buprenorphine HCl from water-base acrylate matrix through human cadaver skin.

| Patch # | Patch Composition | Av Flux ($\mu$g/cm$^2$/hr) | Average Cumulative Bup-HCl Released After 48 Hours ($\mu$g/cm$^2$) |
|---|---|---|---|
| 1 | 2% Bup - 98% water-base | 0.06 ± 0.01 | 2.58 ± 0.51 |

TABLE 9-continued

Flux and cumulative amount of buprenorphine HCl from water-base acrylate matrix through human cadaver skin.

| Patch # | Patch Composition | Av Flux ($\mu g/cm^2/hr$) | Average Cumulative Bup-HCl Released After 48 Hours ($\mu g/cm^2$) |
|---|---|---|---|
|  | acrylate |  |  |
| 2 | 2% Bup + 6% PGML + 2% Capric Acid + 90% polymer | 0.35 ± 0.07 | 15.06 ± 4.30 |
| 3 | 2% Bup + 6% PGML + 2% Oleic acid + 90% polymer | 0.31 ± 0.05 | 13.04 ± 2.70 |
| 4 | 2% Bup + 6.1% PGM + 2% Softgen + 90% polymer | 0.30 ± 0.02 | 5.50 ± 0.60 |
| 5 | 2% Bup + 6% PGML + 2% Transcutol + 90% polymer | 0.15 ± 0.01 | 6.42 ± 0.33 |

An in vitro skin flux experiment was conducted following the same procedure as explained in Example 1.

The average flux and cumulative amount of buprenorphine HCl released after 48 hours is tabulated in Table 9. The flux and cumulative amount of buprenorphine HCl was significantly increased due to PGML.

Example 7

5% Buprenorphine HCl+5% PGML+10% Enhancer—Water based Acrylate

A series of 5% Buprenorphine HCl plus 5% PGML plus 10% Enhancer—water based acrylate patches were prepared by the following procedure: The 5% Buprenorphine HCl was mixed and sonicated with 5% PGML for 10 minutes. The appropriate amount of the drug enhancer mixture was then added to a solution of water based acrylate and rotated for about 10 hours. The drug-PGML-enhancer-polymer mixture was then casted on a polyester film (#1072 release liner) with a 10 mil knife. The solvent in the polymer solution was evaporated in a 75° C. oven for 2 hours. The resulting polymer films were laminated with another polyester film. The composition of each system is shown in Table 10.

TABLE 10

Flux and Cumulative amount of Buprenorphine HCl from water-base acrylate matrix through human cadaver skin.

| # | Patch Composition | Av. Flux ($\mu g/cm^2/hr$) | Average Cumulative Bup HCl Released After 48 Hours ($\mu g/cm^2/hr$) |
|---|---|---|---|
| Gelva ® 2333 Polymer | | | |
| 1) | 5% Bup HCl + 5% PGML + 10% Capric Acid | 0.96 ± 0.09 | 41.31 ± 3.8 |
| 2) | 5% Bup HCl + 5% PGML + 5% Capric Acid | 0.78 ± 0.06 | 33.90 ± 2.5 |
| 3) | 5% Bup HCl + 5% PGML + 5% Capric Acid | 0.75 ± 0.03 | 31.96 ± 1.4 |
| 4) | 5% Bup HCl + 5% PGML + 5% Oleic Acid | 0.67 ± 0.06 | 29.72 ± 2.7 |

These materials gave the best flux values seen to date and thus are preferred.

I claim:

1. A laminated composite for administering buprenorphine hydrochloride to an individual transdermally comprising:
    (a) a polymer backing layer that is substantially impermeable to buprenorphine hydrochloride; and
    (b) a reservoir layer comprising a water-base acrylate pressure-sensitive adhesive, 1 to 12% by weight buprenorphine hydrochloride and 2 to 25% by weight of a permeation enhancer comprising propylene glycol monolaurate in combination with capric acid or oleic acid, wherein the skin contact area of the composite is 10 to 100 cm$^2$ and the rate of administration from the composite is about 1 to about 100 $\mu$g/hr.

2. The laminated composite of claim 1 wherein the buprenorphine hydrochloride constitutes 1 to 12% by weight of the reservoir and the permeation enhancer constitutes 2 to 20% by weight of the reservoir.

3. The laminated composite of claim 1 wherein the buprenorphine hydrochloride constitutes 5% by weight of the reservoir, the propylene glycol monolaurate constitutes 5% by weight of the reservoir and the capric or oleic acid constitutes 5% to 10% by weight of the reservoir.

4. A method for providing buprenorphine hydrochloride therapy to an individual in need of such therapy comprising affixing the laminated composite of claim 1 to the skin of said individual.

5. A method for providing buprenorphine hydrochloride therapy to an individual in need of such therapy comprising affixing the laminated composite of claim 2 to the skin of said individual.

6. A method for providing buprenorphine hydrochloride therapy to an individual in need of such therapy comprising affixing the laminated composite of claim 3 to the skin of said individual.

* * * * *